United States Patent [19]

Seacord

[11] Patent Number: 4,971,056
[45] Date of Patent: Nov. 20, 1990

[54] ARCUATE SHAPED COOLING JACKET

[75] Inventor: Alan R. Seacord, Chula Vista, Calif.
[73] Assignee: Daily Medical Products Incorporated, San Diego, Calif.
[21] Appl. No.: 390,084
[22] Filed: Aug. 7, 1989
[51] Int. Cl.$^5$ .............................................. A61F 7/00
[52] U.S. Cl. .................................. 128/401; 128/400; 165/46
[58] Field of Search ....................... 128/402, 400, 401; 62/530; 165/46

[56] References Cited

U.S. PATENT DOCUMENTS

| 2,726,658 | 12/1955 | Chessey | 128/400 |
| 3,091,242 | 5/1963 | Johnson et al. | 128/402 |
| 3,717,199 | 2/1973 | Dienst | 128/401 |
| 3,738,372 | 6/1973 | Shioshvili | 128/402 |
| 3,830,676 | 8/1974 | Elkins | 156/289 |
| 4,108,146 | 8/1978 | Golden | 128/402 |
| 4,149,541 | 4/1979 | Gammons et al. | 128/400 |
| 4,154,245 | 5/1979 | Daily | 128/402 |
| 4,259,961 | 4/1981 | Hood, III | 128/400 |
| 4,416,281 | 11/1983 | Cooper et al. | 128/400 |
| 4,605,006 | 8/1986 | Jacques | 128/403 |

FOREIGN PATENT DOCUMENTS 1448068 9/1976 United Kingdom .

OTHER PUBLICATIONS

Cobe Laboratories advertising flyer, COBE TCD Topical Cooling Device.

Primary Examiner—Edward M. Coven
Assistant Examiner—Mark S. Graham
Attorney, Agent, or Firm—Baker, Maxham, Jester & Meador

[57] ABSTRACT

A flexible thermal jacket of a generally thin flat arcuate configuration, having a heat transfer face and an insulating face, for forming around and thermally contacting an organ and circulating a thermal fluid for controlling the temperature of the organ comprises, a first sheet of thin pliable flexible impervious material having an arcuate configuration defined by radially extending side edges and by inner and outer arcuate edges extending between the side edges, a second sheet substantially identical to the first sheet, the first sheet overlying and sealingly bonded to the second sheet along the arcuate edges thereof and along lines defining an elongated serpentine fluid passage extending throughout the area of the sheets between adjacent inlet and outlet ports opening outward from the outer arcuate edge adjacent one of the side edges of the sheet.

16 Claims, 2 Drawing Sheets

ARCUATE SHAPED COOLING JACKET

BACKGROUND OF THE INVENTION

The present invention relates to thermal cooling devices and pertains particularly to an improved cooling jacket for cooling of the heart or other organs during surgical operations.

It is desirable to reduce the metabolism of organs when they are being operated on. In cardiac surgery, for example, the heart is often deprived of blood for at least a short period of time. If the energy requirements of the heart are sufficiently reduced during this time, damage to the heart can be reduced or eliminated. A desireable approach to reducing the energy requirements of the heart and other organs is to reduce the temperature of the organ.

Several methods of cooling organs of the body during surgery have been developed. One of the desirable approaches is that of using a cooling jacket or pad, such as disclosed in U.S. Pat. No. 4,154,245, entitled "Apparatus for Local Hypothermia", of common assignment herewith and incorporated herein by reference as though fully set forth. While these known designs for cooling jackets are generally satisfactory, they have a number of drawbacks. One problem of the prior art devices is that it is difficult to conform them to close fitting configuration with the heart. Another problem is that the fluid lines which carry cooling fluid to and from the jacket are located at opposite ends of the jacket and interfere with manipulation and use of the jacket.

Accordingly it is desireable that improved cooling jackets be available.

SUMMARY AND OBJECTS OF THE INVENTION

It is the primary object of the present invention to provide an improved cooling jacket for local hypothermia.

BRIEF DESCRIPTION OF THE DRAWING

The above and other objects and advantages of the present invention will become apparent from the following description when read in conjunction with the drawings wherein.

DETAILED DESCRIPTION OF A PREFERRED EMBODIMENT

Figure 1:
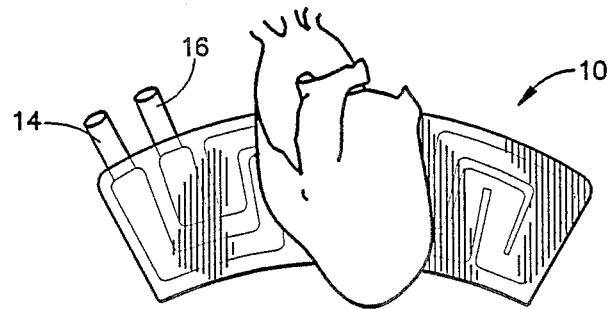
FIG. 1 is a top plan view illustrating the invention in use.

Referring to FIG. 1 of the drawings, there is illustrated a cooling jacket in accordance with the invention, designated generally by the numeral 10, shown in position underneath a heart 12, in the process of wrapping around the heart for applying hypothermia thereto. The cooling jacket, as illustrated, has an arcuate or fan shape, such that when rolled it forms a frustrum of a cone, thereby forming a cup shape configuration encompassing the heart.

The cooling jacket is also provided with inlet and outlet tubes or ports 14 and 16, which are at one end and extend outward from the outermost curved edge of the jacket. The placement of these inlet and outlet ports or cooling fluid supply and return tubes at one end of the jacket, and at the outside diameter of the jacket leaves the remainder of the jacket unobstructed. This places the tubes out of the way to enable the jacket to be inserted and slipped beneath the heart and the free end wrapped around the heart. The tubes are thus placed in a position where they do not interfere with placement of the jacket in and around the heart.

The pad 10, as illustrated, is thin and flat and of an arcuate or fan shape, having an outer arcuate edge 18 and an inner arcuate edge 20, with a left radial edge 22 and a right radial edge 24. This shape of the jacket enables it to be rolled in a cup-like frustoconical configuration to best fit the shape of the heart and provide maximum and most efficient contact therewith. The cooling jacket with this configuration can be more closely conformed to the shape of the lower portion of the heart.

Figure 2:
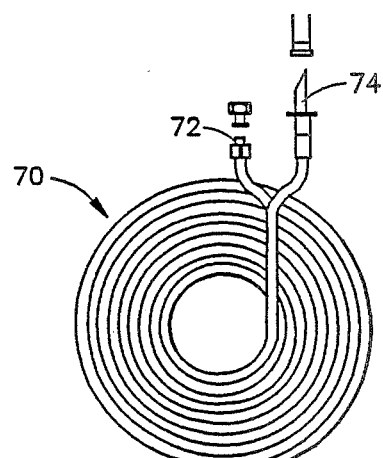
FIG. 2 is a top plan view of the cooling jacket in combination with a coil.
Figure 2:
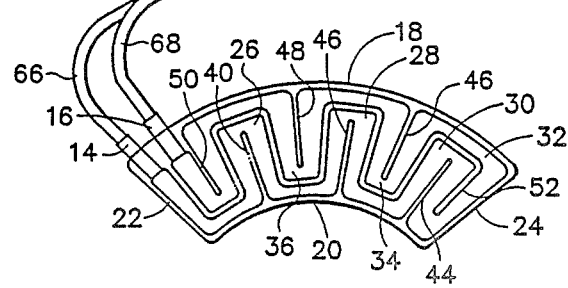

As illustrated in FIG. 2, the jacket or pad has an upper cooling surface with underlying cooling fluid channels, with there being supply and return channels with, for example, supply channel being formed with a plurality or series of U-shaped channels 26, 28 and 30 extending from the inlet port 14 into return channel 32, also having alternate U-shaped channels 34, 36 and 38. These flow channels are formed by a plurality of inwardly extending finger or line welds or seams 40, 42 and 44, extending inward from a seam weld along the inner edge or diameter 20. Similar finger or line welds 46, 48 and 50 extend inward from the outer edge 18.

A central serpentine weld 52 alternates across the jacket from between the inlet and outlet ports 14 and 16 and at the edge 22 over to adjacent the edge 24. This forms alternating channels across the length of the pad, alternating between the supply and return channel. This serpentine array of the supply and return fluid passages or channels provides a more uniform temperature distribution across the cooling face of the channel. The result is adjacent counter flow channels that maintain a more uniform temperature across the entire face of the jacket.

Figure 3:
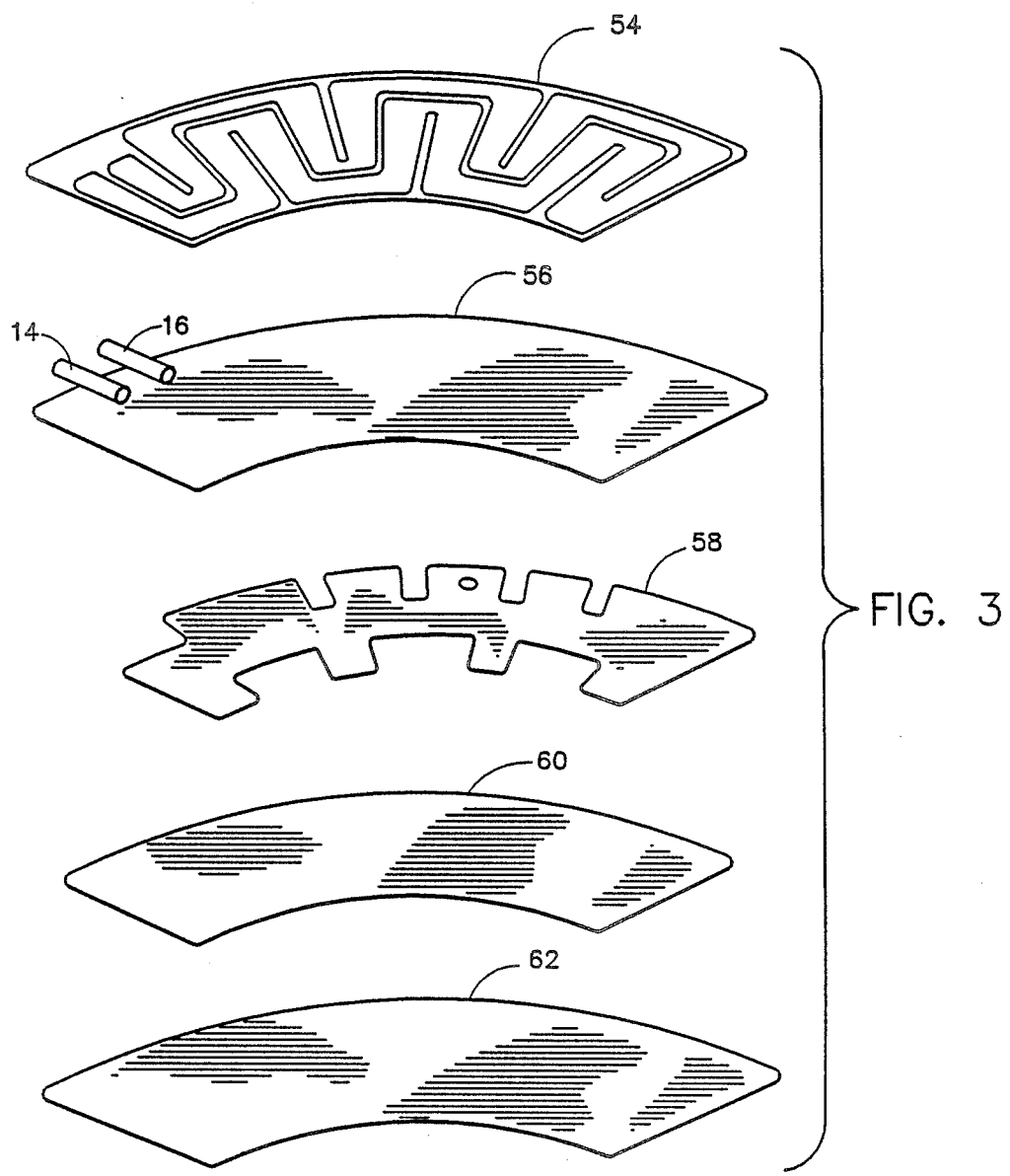
FIG. 3 is an exploded view illustrating details of construction of the cooling jacket.

Referring to FIG. 3 of the drawings, there are illustrated details of the structure and steps of construction of the jacket in accordance with the invention. In accordance with the invention as illustrated in FIG. 3, the cooling jacket is made up of a plurality of layers, as will be illustrated and described. The cooling jacket comprises, as illustrated, a top cover, designated generally by the numeral 54, which has the characteristic fan or arcuate shape and is constructed of a suitable pliable impervious material, such as a good medical grade of silicone or urethane, preferably on the order of about two to six mils in thickness. This cover may be plain or it may have the characteristic weld pattern as illustrated. A backing cover 56 of a similar size, shape and material, as the top cover is placed beneath the cover 54, and is provided with tubes 14 and 16 defining the inlet and outlet ports at one end.

In the process of assembly, the top cover 54 is placed over the bottom cover 56, with the tubing joints 14 and 16 in position and an RF 2 welder is applied to weld the top and bottom covers together along the inner and outer arcuate edges 18 and 20, and along the inner weld lines as illustrated, thereby forming the cooling fluid channels in the jacket.

A backbone member 58, which is preferably formed of a thin sheet of aluminum or the like for example on the order of about thirty-two thousandth of an inch in thickness, can be shaped and retain its shape to support the jacket in a selected position or shape. This backbone is selected and assembled behind the back cover 56, with a foam insulating pad 60 of the characteristic arcuate shape then selected and placed over the backbone 58. A backing cover 62 of substantially the same characteristic, size and shape as the first backing cover 56 selected and placed over the backbone and foam padding 60. The cover 62 is slightly larger than the foam backing 62, and is welded along the perimeter or peripheral edge to the cover 56, encasing the backbone 58 and the insulating pad 60. The insulating pad 60 may be of any suitable insulating foam having a thickness of on the order of about 10–40 mil. The jacket may be formed in selected sizes for use on different size hearts.

In use a cooling jacket of an appropriate size is selected and placed around the heart and is connected to a source of circulating cooling fluid. The jacket is connected by means of lines of tubes 66 and 68, which may be in a closed loop for example with a pump, a cooling unit or ice pack, and with suitable means for adjusting the coolant flow. The tubes 66 and 68 may be formed in a pan coil 70 which may be placed in an ice bath or the like with ends 72 and 74 connected to a source of cooling fluid. A suitable fluid may be a sterile saline solution contained in a standard I.V. bag and immersed in an ice water bath. A suitable pump circulates the cooling fluid through the system.

While I have illustrated and described my invention by means of specific embodiments, it is to be understood that numerous changes and modifications may be made therein without departing from the spirit and scope of the invention as defined in the appended claims.

I claim:

1. A flexible thermal pad of a generally thin flat arcuate configuration, having a heat transfer face and an insulating face, for forming around and thermally contacting an organ and circulating a thermal fluid for controlling the temperature of the organ comprising:
    a first sheet of thin pliable flexible fluid impervious material having an arcuate configuration defined by peripheral edge including inner and outer arcuate edges;
    a second sheet substantially identical to said first sheet, said first sheet overlying and sealingly bonded to said second sheet along the peripheral edges thereof and along lines defining an elongated serpentine fluid passage extending throughout the area of said first and second sheets between adjacent inlet and outlet ports at one end and opening outward from said outer arcuate edge of said first and second sheets.

2. A flexible thermal pad according to claim 1 wherein:
    said first and second sheets are bonded together along a serpentine line extending from a portion between said inlet and outlet ports at one side edge to a portion adjacent a second side edge thereof.

3. A flexible thermal pad according to claim 1 wherein:
    said sheets are additionally connected together along lines extending radially inward from said outer arcuate edge and radially outward from said inner arcuate edge.

4. A flexible thermal pad according to claim 1 and further comprising:
    a backing sheet; and
    an insulating sheet disposed between said second sheet and said backing sheet.

5. A flexible thermal pad according to claim 4 and comprising:
    a malleable plate disposed between said second sheet and said backing sheet.

6. A flexible thermal pad according to claim 2 wherein:
    said first and second sheets are additionally bonded together along lines extending radially inward from said outer arcuate edge and radially outward from said inner arcuate edge.

7. A flexible thermal pad according to claim 6 and further comprising:
    a backing sheet; and
    an insulating sheet disposed between said second sheet and said backing sheet.

8. A flexible thermal pad according to claim 7 and comprising:
    a malleable plate disposed between said second sheet and said backing sheet.

9. A flexible thermal jacket of a generally thin flat arcuate configuration, having a heat transfer face and an insulating face, for forming around and thermally contacting an organ and circulating a thermal fluid for controlling the temperature of the organ comprising:
    a first sheet of thin pliable flexible fluid impervious material having an arcuate configuration defined by radially extending side edges and by inner and outer arcuate edges extending between said side edges and defining a heat transfer face;
    a second backing sheet substantially identical to said first sheet, said first sheet overlying said second sheet and sealingly bonded thereto along said side edges and said arcuate edges thereof and along lines defining an elongated serpentine fluid passage extending back and forth between said arcuate edges throughout the area of said first and second sheets between adjacent inlet and outlet ports opening outward from said outer arcuate edge adjacent one of said side edges of said first and second sheets.

10. A flexible thermal pad according to claim 9 wherein:
    said first and second sheets are bonded together along a serpentine line extending from a position between said inlet and outlet ports adjacent said one side edge to a position adjacent another side edge thereof; and,
    said first and second sheets are additionally bonded together along lines extending radially inward from said outer arcuate edge and radially outward from said inner arcuate edge.

11. A flexible thermal pad according to claim 10 and further comprising:
    a backing sheet of thin pliable fluid impervious material; and
    an insulating sheet of urethane foam disposed between said first sheet and said backing sheet.

12. A flexible thermal pad according to claim 11 and comprising:
    a malleable plate disposed between said first sheet and said backing sheet.

13. A flexible thermal jacket of a generally thin flat arcuate configuration, having a heat transfer face and an insulating face, for forming around and thermally contacting an organ and circulating a thermal fluid for controlling the temperature of the organ comprising:

a first sheet of thin pliable flexible fluid impervious material having an arcuate configuration defined by radially extending side edges and by inner and outer arcuate edges extending between said side edges;

a second sheet substantially identical to said first sheet, said first sheet overlying and sealingly bonded to said second sheet along the said arcuate edges thereof and along a serpentine line and lines extending radially inward and outward respectively from said outer and inner arcuate edges defining an elongated serpentine fluid passage extending back and forth throughout the area of said first and second sheets between adjacent inlet and outlet ports opening outward from said outer arcuate edge adjacent one of said side edges of said first and second sheets.

14. A flexible thermal pad according to claim 13 and further comprising:
   a backing sheet of thin pliable fluid impervious material;
   an insulating sheet of urethane foam disposed between said second sheet and said backing sheet; and
   a malleable plate disposed between said sheet of urethane foam and said second sheet.

15. A flexible thermal pad according to claim 14 wherein:
   said first and said second sheets are constructed of polyurethane of about two to six mils in thickness; and said sheet of urethane foam is on the order of about ten thousandths of an inch in thickness.

16. A flexible thermal pad according to claim 15 wherein:
   said malleable plate is a sheet of aluminum of on the order of about thirty two thousandths of an inch in thickness.

* * * * *